United States Patent
Kwak et al.

(10) Patent No.: US 7,766,940 B2
(45) Date of Patent: Aug. 3, 2010

(54) POSTERIOR STABILIZATION SYSTEM

(75) Inventors: Seungkyu Daniel Kwak, Grafton, MA (US); Amie Borgstrom, North Attleborough, MA (US); John Riley Hawkins, Cumberland, RI (US); William Dunbar, Norton, MA (US)

(73) Assignee: DePuy Spine, Inc., Raynham, MA (US)

( * ) Notice: Subject to any disclaimer, the term of this patent is extended or adjusted under 35 U.S.C. 154(b) by 476 days.

(21) Appl. No.: 10/905,376

(22) Filed: Dec. 30, 2004

(65) Prior Publication Data

US 2006/0149230 A1   Jul. 6, 2006

(51) Int. Cl.
*A61B 17/70* (2006.01)
(52) U.S. Cl. ............................ 606/247; 606/246
(58) Field of Classification Search ............... 606/61
See application file for complete search history.

(56) References Cited

U.S. PATENT DOCUMENTS

| | | | |
|---|---|---|---|
| 3,648,691 A | 3/1972 | Lumb et al. |
| 3,693,616 A | 9/1972 | Roaf et al. |
| 4,448,191 A | 5/1984 | Rodnyansky et al. |
| 4,743,260 A | 5/1988 | Burton |
| 5,084,049 A | 1/1992 | Asher et al. |
| 5,092,866 A | 3/1992 | Breard |
| 5,152,303 A | 10/1992 | Allen |
| 5,176,680 A | 1/1993 | Vignaud et al. |
| 5,190,543 A | 3/1993 | Schlapfer |
| 5,261,911 A | 11/1993 | Carl |
| 5,282,863 A | 2/1994 | Burton |
| 5,306,275 A | 4/1994 | Bryan |
| 5,360,429 A | 11/1994 | Jeanson et al. |
| 5,375,823 A | 12/1994 | Navas et al. |
| 5,387,213 A | 2/1995 | Breard |
| 5,403,316 A | 4/1995 | Ashman |

(Continued)

FOREIGN PATENT DOCUMENTS

EP   0576379 A1   12/1993

(Continued)

OTHER PUBLICATIONS

EP Search Report, Application No. 05849737.1, Aug. 6, 2009.

*Primary Examiner*—Eduardo C Robert
*Assistant Examiner*—Mary Hoffman
(74) *Attorney, Agent, or Firm*—Nutter McClennen & Fish LLP (57) ABSTRACT

Various methods and devices for replacing damaged, injured, diseased, or otherwise unhealthy posterior elements, are provided. In one exemplary embodiment, a posterior implant is provided and can be adapted to control movement of two or more adjacent vertebrae. In particular, the implant can be adapted to control extension, flexion, and lateral bending of adjacent vertebrae. The implant can also be adapted to substantially prevent rotation of the adjacent vertebrae. In another exemplary embodiment, the implant can have an envelope of motion that is within an envelope of motion of a disc, either natural or artificial, that is disposed between adjacent vertebrae. In other words, the implant can be configured to allow flexion, extension, lateral bending of the vertebrae to within the amount of flexion, extension, and lateral bending allowed by the particular disc. The implant can also be adapted to substantially prevent rotation of the vertebrae relative to one another.

6 Claims, 8 Drawing Sheets

U.S. PATENT DOCUMENTS

| | | |
|---|---|---|
| 5,415,661 A | 5/1995 | Holmes |
| 5,425,732 A | 6/1995 | Ulrich et al. |
| 5,437,669 A | 8/1995 | Yuan et al. |
| 5,437,671 A | 8/1995 | Lozier et al. |
| 5,474,086 A | 12/1995 | McCormick et al. |
| 5,486,174 A | 1/1996 | Fournet-Fayard et al. |
| 5,496,318 A | 3/1996 | Howland et al. |
| 5,540,688 A | 7/1996 | Navas |
| 5,556,431 A | 9/1996 | Buttner-Janz |
| 5,562,737 A | 10/1996 | Graf |
| 5,571,191 A | 11/1996 | Fitz |
| 5,591,165 A * | 1/1997 | Jackson .................. 606/264 |
| 5,601,554 A | 2/1997 | Howland et al. |
| 5,672,175 A | 9/1997 | Martin |
| 5,681,312 A | 10/1997 | Yuan et al. |
| 5,716,355 A | 2/1998 | Jackson |
| 5,725,582 A | 3/1998 | Bevan et al. |
| 5,733,284 A | 3/1998 | Martin et al. |
| 5,755,796 A | 5/1998 | Ibo et al. |
| 5,766,254 A | 6/1998 | Gelbard |
| 5,810,815 A | 9/1998 | Morales et al. |
| RE36,221 E | 6/1999 | Breard |
| 5,928,233 A | 7/1999 | Apfelbaum et al. |
| 5,938,663 A | 8/1999 | Petreto |
| 5,961,516 A | 10/1999 | Graf |
| 6,019,760 A | 2/2000 | Metz-Stavenhagen et al. |
| RE36,758 E | 6/2000 | Fitz |
| 6,132,464 A | 10/2000 | Martin |
| 6,241,730 B1 | 6/2001 | Alby |
| 6,248,106 B1 | 6/2001 | Ferree |
| 6,267,764 B1 | 7/2001 | Elberg |
| 6,273,888 B1 | 8/2001 | Justis |
| 6,355,038 B1 | 3/2002 | Pisharodi |
| 6,364,883 B1 | 4/2002 | Santilli |
| 6,419,703 B1 | 7/2002 | Fallin |
| 6,440,169 B1 | 8/2002 | Elberg et al. |
| 6,468,276 B1 | 10/2002 | McKay |
| 6,547,790 B2 | 4/2003 | Harkey |
| 6,551,322 B1 * | 4/2003 | Lieberman ............. 606/246 |
| 6,551,332 B1 | 4/2003 | Nguyen et al. |
| 6,554,831 B1 | 4/2003 | Rivard |
| 6,554,832 B2 | 4/2003 | Shluzas |
| 6,565,605 B2 | 5/2003 | Goble |
| 6,579,319 B2 | 6/2003 | Goble |
| 6,610,091 B1 | 8/2003 | Reiley |
| 6,626,904 B1 | 9/2003 | Jammet et al. |
| 6,626,909 B2 | 9/2003 | Chin |
| 6,626,944 B1 | 9/2003 | Taylor |
| 6,645,207 B2 | 11/2003 | Dixon |
| 6,669,729 B2 | 12/2003 | Chin |
| 6,811,567 B2 | 11/2004 | Reiley |
| 7,011,685 B2 | 3/2006 | Arnin et al. |
| 7,074,237 B2 | 7/2006 | Goble et al. |
| 7,104,992 B2 | 9/2006 | Bailey |
| 7,189,236 B2 | 3/2007 | Taylor et al. |
| 7,270,665 B2 | 9/2007 | Morrison et al. |
| 2002/0029039 A1 | 3/2002 | Zucherman et al. |
| 2002/0055740 A1 | 5/2002 | Lieberman |
| 2002/0065557 A1 | 5/2002 | Goble |
| 2002/0072800 A1 | 6/2002 | Goble |
| 2002/0123806 A1 | 9/2002 | Reiley |
| 2002/0133155 A1 | 9/2002 | Ferree |
| 2002/0151978 A1 | 10/2002 | Zacouto et al. |
| 2003/0004572 A1 | 1/2003 | Goble |
| 2003/0028250 A1 | 2/2003 | Reiley |
| 2003/0055427 A1 | 3/2003 | Graf |
| 2003/0083657 A1 | 5/2003 | Drewry |
| 2003/0093078 A1 | 5/2003 | Ritland |
| 2003/0109880 A1 | 6/2003 | Shirado |
| 2003/0135277 A1 | 7/2003 | Bryan et al. |
| 2003/0153912 A1 | 8/2003 | Graf |
| 2003/0171749 A1 | 9/2003 | Le Couedic |
| 2003/0171750 A1 | 9/2003 | Chin |
| 2003/0176926 A1 * | 9/2003 | Boehm et al. ............. 623/17.16 |
| 2003/0187438 A1 | 10/2003 | Assaker et al. |
| 2003/0187454 A1 | 10/2003 | Gill et al. |
| 2003/0191470 A1 | 10/2003 | Ritland |
| 2003/0191532 A1 | 10/2003 | Goble |
| 2003/0220642 A1 | 11/2003 | Freudiger |
| 2003/0220643 A1 * | 11/2003 | Ferree .................. 606/61 |
| 2004/0002708 A1 | 1/2004 | Ritland |
| 2004/0006391 A1 | 1/2004 | Reiley |
| 2004/0015174 A1 | 1/2004 | Null et al. |
| 2004/0049189 A1 | 3/2004 | Le Couedic |
| 2004/0049190 A1 | 3/2004 | Biedermann |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0097950 A1 | 5/2004 | Foley et al. |
| 2004/0111154 A1 | 6/2004 | Reiley |
| 2004/0116927 A1 | 6/2004 | Graf |
| 2004/0127989 A1 * | 7/2004 | Dooris et al. ............. 623/13.17 |
| 2004/0133203 A1 | 7/2004 | Young et al. |
| 2004/0138660 A1 | 7/2004 | Serhan |
| 2004/0143264 A1 | 7/2004 | McAfee |
| 2004/0147928 A1 | 7/2004 | Landry et al. |
| 2004/0186475 A1 | 9/2004 | Falahee |
| 2004/0186575 A1 * | 9/2004 | Varga et al. ............. 623/17.11 |
| 2004/0236329 A1 | 11/2004 | Panjabi |
| 2004/0249379 A1 | 12/2004 | Winslow et al. |
| 2004/0267259 A1 | 12/2004 | Mazda et al. |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0033439 A1 * | 2/2005 | Gordon et al. ........... 623/17.16 |
| 2005/0049708 A1 | 3/2005 | Atkinson et al. |
| 2005/0055096 A1 * | 3/2005 | Serhan et al. ............. 623/17.11 |
| 2005/0101954 A1 | 5/2005 | Simonson |
| 2005/0101956 A1 | 5/2005 | Simonson |
| 2005/0113927 A1 | 5/2005 | Malek |
| 2005/0119748 A1 | 6/2005 | Reiley et al. |
| 2005/0131409 A1 * | 6/2005 | Chervitz et al. ............. 606/61 |
| 2005/0171610 A1 | 8/2005 | Humphreys et al. |
| 2005/0203518 A1 | 9/2005 | Biedermann et al. |
| 2005/0228381 A1 | 10/2005 | Kirschman |
| 2005/0228501 A1 | 10/2005 | Miller et al. |
| 2005/0240265 A1 | 10/2005 | Kuiper et al. |
| 2005/0245929 A1 | 11/2005 | Winslow et al. |
| 2005/0256578 A1 | 11/2005 | Blatt et al. |
| 2005/0277922 A1 * | 12/2005 | Trieu et al. ................ 606/61 |
| 2005/0277930 A1 * | 12/2005 | Parsons .................. 606/61 |
| 2006/0036240 A1 | 2/2006 | Colleran et al. |
| 2006/0052785 A1 | 3/2006 | Augostino et al. |
| 2006/0079896 A1 | 4/2006 | Kwak et al. |
| 2006/0084976 A1 | 4/2006 | Borgstrom et al. |
| 2006/0084984 A1 * | 4/2006 | Kim ..................... 606/61 |
| 2006/0084991 A1 | 4/2006 | Borgstrom et al. |
| 2006/0129239 A1 * | 6/2006 | Kwak .................. 623/17.13 |
| 2006/0149229 A1 | 7/2006 | Kwak et al. |
| 2006/0149230 A1 | 7/2006 | Kwak et al. |
| 2006/0189983 A1 | 8/2006 | Fallin et al. |
| 2006/0200130 A1 | 9/2006 | Hawkins et al. |
| 2006/0241771 A1 | 10/2006 | Gordon et al. |
| 2006/0265074 A1 | 11/2006 | Krishna et al. |

| | | | |
|---|---|---|---|
| 2006/0271046 A1 | 11/2006 | Kwak et al. | |

FOREIGN PATENT DOCUMENTS

| | | |
|---|---|---|
| EP | 0669109 | 2/1994 |
| EP | 0612507 A1 | 8/1994 |
| EP | 0669109 A1 | 8/1995 |
| EP | 1153577 | 11/2001 |
| FR | 2694182A A1 | 2/1994 |
| FR | 2697428 A1 | 5/1994 |
| FR | 2701833 A1 | 9/1994 |
| WO | WO-01/45576 | 6/2001 |
| WO | WO-02/17803 | 3/2002 |
| WO | WO-02/43603 | 6/2002 |
| WO | WO-02/102259 | 12/2002 |
| WO | WO-03/007828 | 1/2003 |
| WO | WO-03/009737 | 2/2003 |
| WO | 2004024011 A1 | 3/2004 |
| WO | WO-2004/034916 | 4/2004 |

* cited by examiner

POSTERIOR STABILIZATION SYSTEM

FIELD OF THE INVENTION

The present invention relates to spinal instrumentation, and in particular to various devices that are adapted to mimic the natural function of the structural posterior elements.

BACKGROUND OF THE INVENTION

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. Subsequent surgery may also be required after a laminectomy, as a laminectomy predisposes the patient to instability and may lead to post-laminectomy kyphosis (abnormal forward curvature of the spine), pain, and neurological dysfunction. Damaged, diseased levels in the spine were traditionally fused to one another. While such a technique may relieve pain, it effectively prevents motion between at least two vertebrae. As a result, additional stress may be applied to the adjoining levels, thereby potentially leading to further damage.

More recently, techniques have been developed to restore normal function to the facet joints. One such technique involves covering the facet joint with a cap to preserve the bony and articular structure. Capping techniques, however, are limited in use as they will not remove the source of the pain in osteoarthritic joints. Caps are also disadvantageous as they must be available in a variety of sizes and shapes to accommodate the wide variability in the anatomical morphology of the facets. Caps also have a tendency to loosen over time, potentially resulting in additional damage to the joint and/or the bone support structure containing the cap.

Other techniques for restoring the normal function to the posterior element involve arch replacement, in which superior and inferior prosthetic arches are implanted to extend across the vertebra typically between the spinous process. The arches can articulate relative to one another to replace the articulating function of the facet joints. However, aligning two articulating rigid surfaces for facet replacements can be very difficult given the variations in patient anatomy and various motion required (i.e., flexion, extension, lateral bending, and translations).

Accordingly, there remains a need for improved systems and methods that are adapted to mimic the natural function of the facet joints.

BRIEF SUMMARY OF THE INVENTION

The present invention provides various methods and devices for repairing and/or replacing a facet joint, and optionally for replacing other posterior elements, including, for example, the lamina, the posterior ligaments, and/or other features of a patient's spinal column. In one exemplary embodiment, an implant for stabilizing the spine is provided and it can include a first member that is adapted to couple to a first vertebra and a second member that is adapted to couple to a second vertebra adjacent to the first vertebra. The first and second members can be movable relative to one another such that the implant is adapted to control flexion, extension, and lateral bending of the first and second adjacent vertebrae relative to one another, and it is adapted to substantially prevent axial rotation of the first and second adjacent vertebrae relative to one another.

While various techniques can be used to allow movement between the first and second members, in one exemplary embodiment the first and second members are slidably movable relative to one another. A connecting element can be rotatably coupled to the first member and slidably coupled to the second member. The second member can include an elongate slot formed therein that is adapted to slidably receive at least a portion of the connecting element. The connecting element can have a variety of configurations, but in one exemplary embodiment the connecting element comprises a body having a first end that is adapted to rotatably mate to the first member, and an opposed second end that is adapted to be slidably disposed within the elongate slot in the second member. The second end can, for example, have a hexagonal shape that is adapted to allow limited rotation of the second end within the elongate slot in the second member, thereby controlling lateral bending of the adjacent vertebrae relative to one another.

In another embodiment, the first member can include an elongate central portion with proximal and distal ends and a connecting element disposed on the distal end, and the second member can include an elongate central portion having opposed rails extending between proximal and distal ends thereof and defining an elongate slot for slidably receiving at least a portion of the connecting element. In an exemplary embodiment, the proximal end of the elongate slot has an open configuration to allow the connecting element to be removably disposed therein, and the distal end of the elongate slot has a closed configuration to limit distal movement of the connecting element relative to the second member. In yet another exemplary embodiment, the elongate central portion of the second member can be curved along an axis extending between the proximal and distal ends. The device can also include opposed arms extending from the proximal end of the first member for mating the first member to a vertebra, and opposed arms extending from a substantial distal portion of the second member for mating the second member to an adjacent vertebra. In an exemplary embodiment, the opposed arms on the first member extend in a direction substantially perpendicular to a longitudinal axis of the elongate central portion of the first member, and the opposed arms on the second member each include a first portion that extends substantially perpendicular to a longitudinal axis of the elongate central portion of the second member, and a second portion that extends distally at an angle relative to the first portion.

In yet another exemplary embodiment, a spinal stabilizing kit is provided and it includes a spinal prosthesis that is adapted to be disposed between adjacent vertebrae and that has an artificial disc that is movable relative to the adjacent vertebrae such that the spinal prosthesis has a predetermined envelope of motion, and a posterior implant that is adapted to couple to the adjacent vertebrae and that is adapted to limit movement of the adjacent vertebrae to an envelope of motion that is within the envelope of motion of the spinal prosthesis. The spinal prosthesis can have a variety of configurations, but one exemplary spinal prosthesis can include first and second endplate members, and the artificial disc can be movable disposed between the first and second endplate members. The posterior implant can also have a variety of configurations, but one exemplary implant includes a first member that is adapted to couple to a vertebra, and a second member that is adapted to couple to an adjacent vertebra. The first and second members can be movably coupled to one another. The posterior implant can also include a connecting element coupled to the first member and adapted to be slidably received within an elongate slot formed within the second member such that first and second members slide relative to one another to allow flexion and extension of the adjacent vertebrae relative to one another. In an exemplary embodiment, the connecting element has a limited degree of rotation relative to the elongate slot to allow limited lateral bending of the adjacent vertebrae relative to one another.

In other exemplary embodiments, a method for stabilizing the posterior element in adjacent vertebrae is provided and includes implanting a spinal prosthesis between adjacent vertebrae. The spinal prosthesis can have an artificial disc that is movable relative to the adjacent vertebrae such that the spinal prosthesis has a predetermined envelope of motion. The method further includes coupling a posterior implant to the adjacent vertebrae. In an exemplary embodiment, the posterior implant has an envelope of motion that is within the envelope of motion of the spinal prosthesis such that the posterior implant is adapted to control flexion, extension, and lateral bending of the adjacent vertebrae relative to one another, and to substantially limit axial rotation of the adjacent vertebrae relative to one another. The method can also include, prior to coupling a posterior implant to the adjacent vertebrae, determining a desired envelope of motion of a posterior implant based on an image of the spinal prosthesis disposed between the adjacent vertebrae, and selecting a posterior implant having an envelope of motion that corresponds to the desired envelope of motion. In another exemplary embodiment, coupling a posterior implant to adjacent vertebrae can include coupling a first member to a vertebra, and coupling a second member to an adjacent vertebra. The first and second members can be movably coupled to one another. In yet another exemplary embodiment, implanting a spinal prosthesis between adjacent vertebrae can include positioning first and second endplates with the artificial disc disposed therebetween between the adjacent vertebrae.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides various methods and devices for replacing damaged, injured, diseased, or otherwise unhealthy posterior elements, such as the facet joints, the lamina, the posterior ligaments, and/or other features of a patient's spinal column. In one exemplary embodiment, a posterior implant is provided and it can be adapted to control movement of two or more adjacent vertebrae. In particular, the implant can be adapted to control extension, flexion, and lateral bending of the adjacent vertebrae. The implant can also be adapted to substantially prevent axial rotation of the adjacent vertebrae. In another exemplary embodiment, the implant can have an envelope of motion that is within an envelope of motion of a disc, either natural or artificial, that is disposed between the adjacent vertebrae. In other words, the implant can be configured to allow flexion, extension, and lateral bending of the vertebrae within the amount of flexion, extension, and lateral bending allowed by the particular disc. The implant can also be adapted to substantially prevent rotation of the vertebrae relative to one another.

A person skilled in the art will appreciate that, while the methods and devices are especially configured for use in restoring and/or replacing the facet joints and optionally other posterior elements of a patient's spine, the methods and devices can be used for a variety of other purposes in a variety of other surgical procedures. Moreover, while the methods and devices are discussed herein in conjunction with a spinal prosthesis and a posterior implant having particular configurations, a person skilled in the art will appreciate that the methods and devices can be adapted for use with a variety of spinal prosthesis and that the posterior implant can have a variety of other configurations.

Figure 1A:
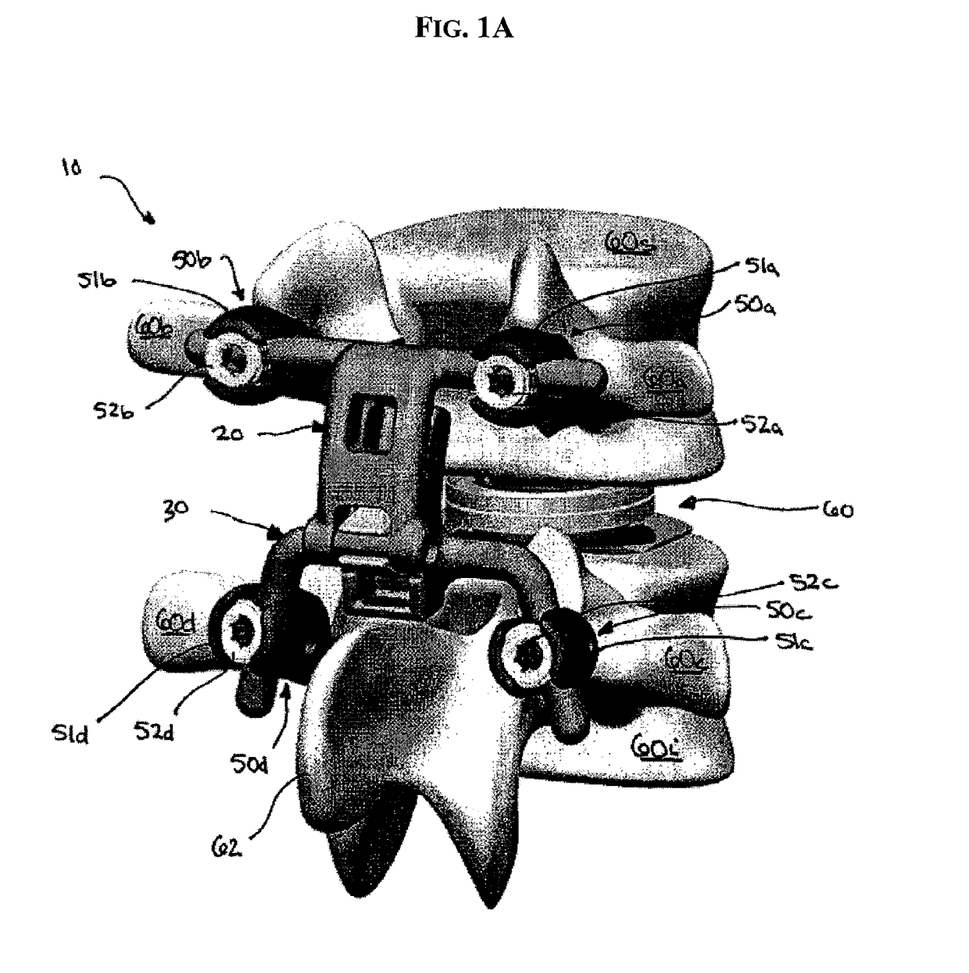
FIG. 1A is a perspective view of one exemplary embodiment of a posterior implant.
Figure 1B:
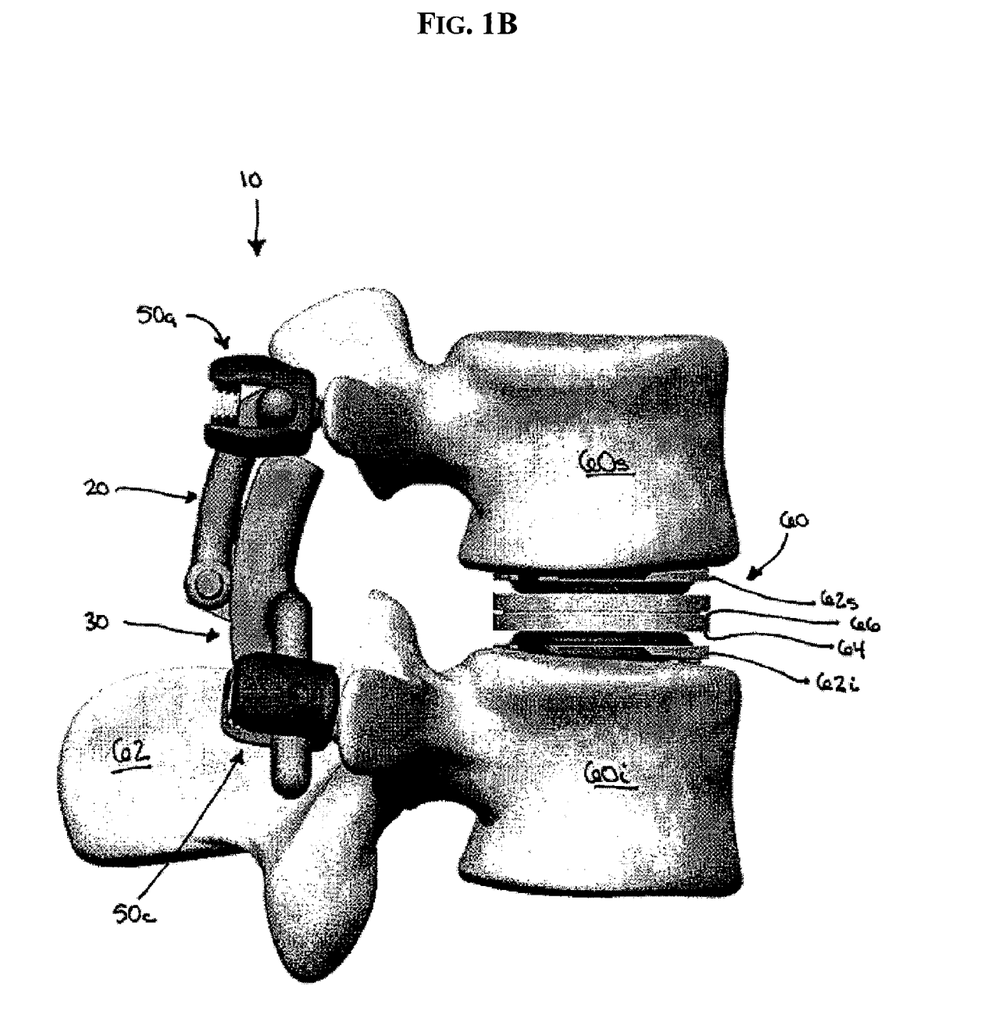
FIG. 1B is a side perspective view of the exemplary posterior implant shown in FIG. 1A.

FIGS. 1A and 1B illustrate one exemplary embodiment of a posterior implant 10. As shown, the implant 10 includes a first member 12 that is adapted to couple to a first vertebra, e.g., a superior vertebra 60s, and a second member 14 that is adapted to couple to a second adjacent vertebra, e.g., an inferior vertebra 60i. One skilled in the art will appreciate that the first and second members can be reversed and the first member can be coupled to the inferior vertebra 60i while the second member can be coupled to the superior vertebra 60s. As is further shown in FIGS. 1A and 1B, the first and second members 20, 30 can be movably coupled to one another such that they are adapted to control movement of the superior and inferior vertebrae 60s, 60i relative to one another. As shown, the first and second members 20, 30 can be slidably coupled to one another to allow flexion and extension of the vertebrae 60s, 60i. The first and second members 20, 30 can also be adapted to rotate relative to one another to allow lateral bending of the first and second vertebrae 60s, 60i relative to one another. Rotation can, however, be substantially prevented in a direction that would allow axial rotation of the vertebrae 60s, 60i relative to one another. In an exemplary embodiment, as indicated above and discussed in more detail below, the implant 10 can have an envelope of motion that is within an envelope of motion of a disc, either natural or artificial, that is disposed between the adjacent vertebrae 60s, 60i. In other words, the implant 10 can be configured to control flexion, extension, and lateral bending of the vertebrae 60s, 60i to certain ranges that are within the amount of flexion, extension, and lateral bending allowed by the particular disc. Such a configuration will allow the posterior implant 10 to work in conjunction with the disc to control movement of the vertebrae 60s, 60i, thereby providing balanced support of spinal motion.

The first member 20 of the exemplary implant 10 can have a variety of configurations. In the illustrated exemplary embodiment, however, the first member 20 is adapted to couple to opposed pedicles 60a, 60b (FIG. 1A) of the superior vertebra 60s and to extend between the pedicles 60a, 60b and inferior to the spinous process (not shown). The configuration of the first member 20 can, however, change depending on whether a laminectomy is performed and the spinous process is present or removed. As shown in more detail in FIGS. 2A-2B, the exemplary first member 20 can be substantially T-shaped and it can include an elongate central portion 24 having proximal and distal ends 24a, 24b, and opposed arms 22a, 22b extending from the elongate central portion 24. The arms 22a, 22b can be adapted to mate to the superior vertebra 60s, and the central portion 24 can be adapted to movably couple to the second member 30.

Figure 2A:
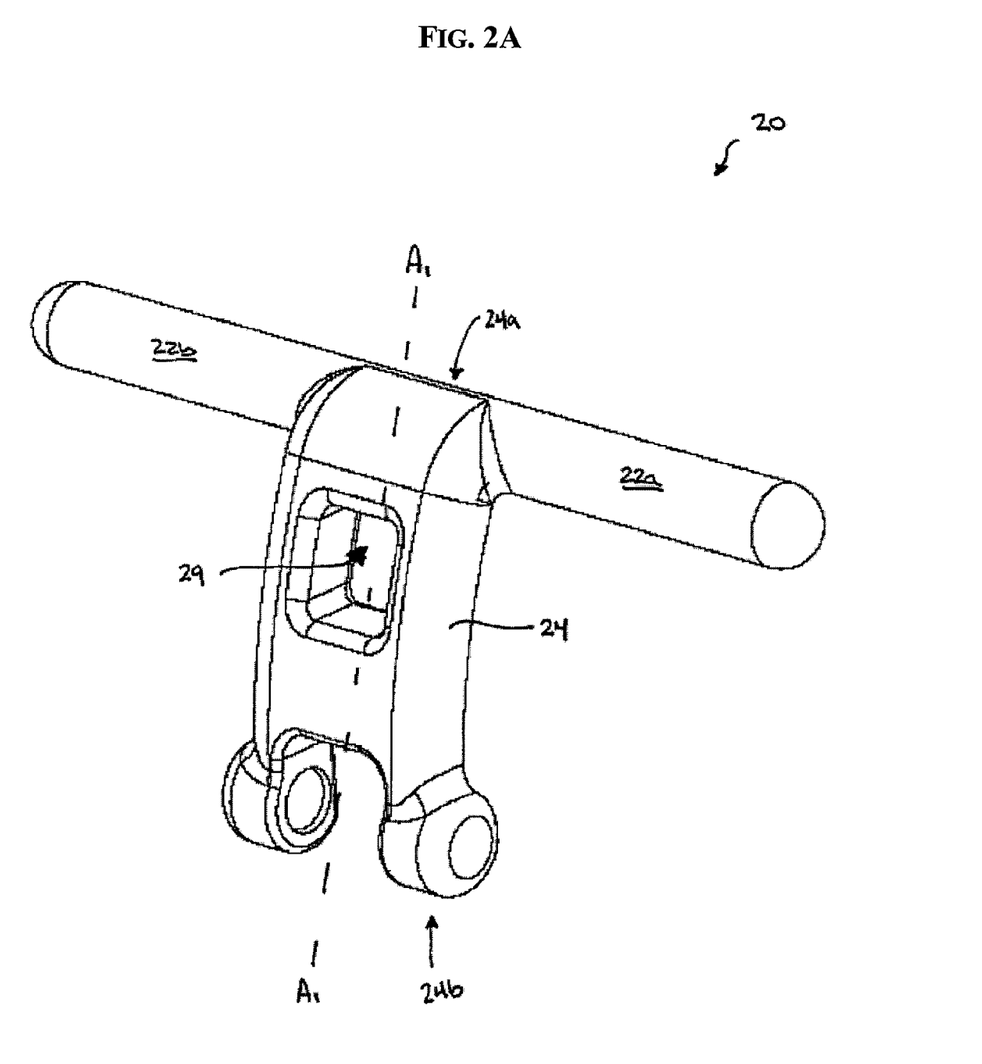
FIG. 2A is a perspective view of a first member of the posterior implant shown in FIGS. 1A and 1B.
Figure 2B:
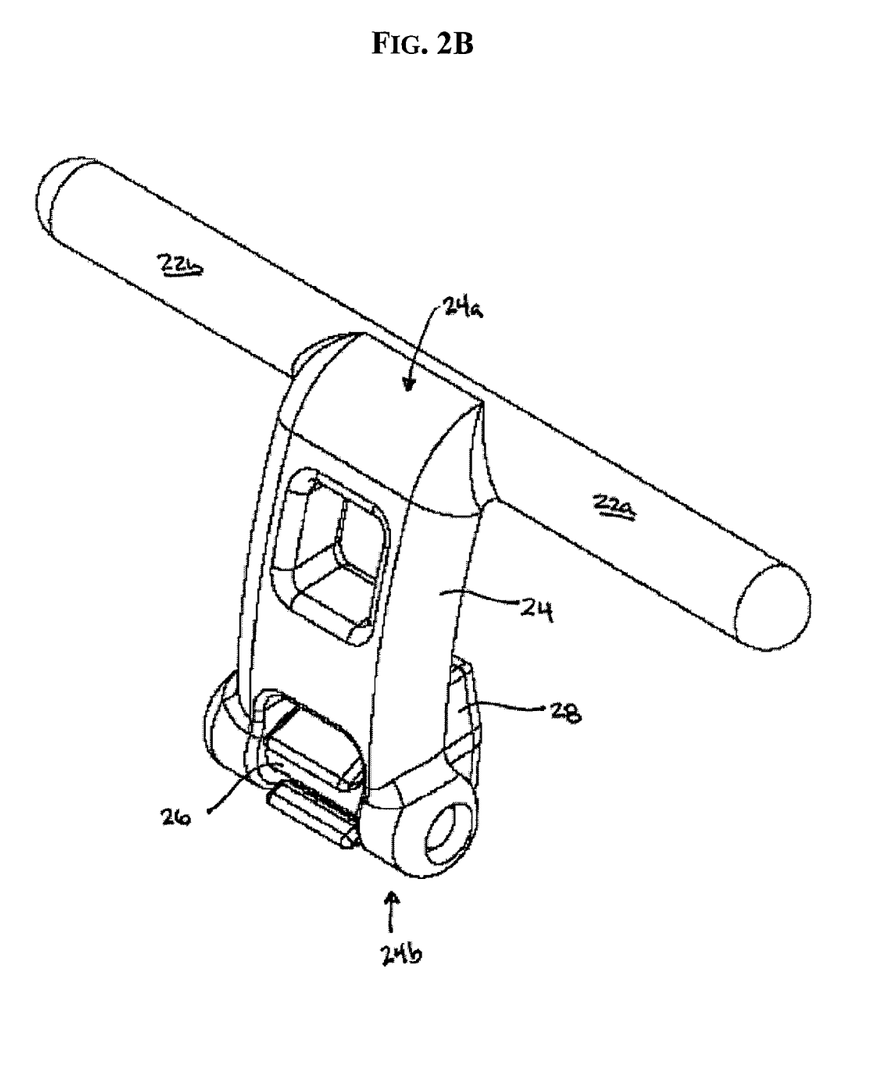
FIG. 2B is a perspective view of the first member shown in FIG. 2A having a connecting element mated thereto.

Each arm 22a, 22b can have a variety of configurations, and the arms 22a, 22b can extend from a variety of locations on the elongate central portion 24. In the illustrated exemplary embodiment, the arms 22a, 22b are rod-shaped and they extend from opposed sides of the proximal end 24a of the elongate central portion 24 in a direction that is substantially perpendicular to a longitudinal axis $A_1$ of the central portion 24. The configuration of each arm 22a, 22b can, however, vary depending on the intended use, and the arms 22a, 22b can be curved or otherwise shaped to facilitate attachment to the vertebra 60s.

As noted above, the arms 22a, 22b are adapted to mate to the superior vertebra 60s. While various techniques can be used to allow the arms 22a, 22b to mate to the vertebra 60s, in the illustrated exemplary embodiment each arm 22a, 22b is adapted to mate to a bone engaging element, such as a bone screw. While virtually any bone screw known in the art can be used, FIGS. 1A and 1B illustrate bone screws 50a, 50b. Each bone screw 50a, 50b has a threaded shank (not shown) that is adapted to extend into the vertebra 60s, and a receiving member 51a, 51b formed on the threaded shank. In an exemplary embodiment, the bone screws 50a, 50b are polyaxial such that the receiving members 51a, 51b can pivot relative to the threaded shank to allow the receiving members 51a, 51b to be adjusted as may be necessary. As shown, each arm 22a, 22b can be positioned within the receiving member 51a, 51b of each bone screw 50a, 50b, and a locking mechanism, such as a locking nut 52a, 52b, can be used to secure the arms 22a, 22b to the bone screws 50a, 50b. A person skilled in the art will appreciate that a variety of devices can be used to attach the arms 22a, 22b to the vertebra 60s, and bone screws 50a, 50b are merely shown for illustration purposes.

The elongate central portion 24 of the first member 20 can also have a variety of configurations, but in an exemplary embodiment, as indicated above, the elongate central portion 24 is adapted to couple to the second member 30, and in particular to an elongate central portion 34 of the second member 30, as will be discussed in more detail below. As shown in FIGS. 2A and 2B, the elongate central portion 24 has a substantially rectangular shape with a proximal end 24a that is coupled to the opposed arms 22a, 22b and a distal end 24b that is adapted to connect to the second member 30. The elongate central portion 24 can also be curved along the longitudinal axis $A_1$ to correspond to a curvature of the elongate central portion 34 of the second member 30, as will be discussed in more detail below. The elongate central portion 24 can also include other features, such as an alignment mechanism to facilitate alignment of the elongate central portion 24 of the first member 20 with the elongate central portion 34 of the second member 30. By way of non-limiting example, the alignment mechanism can be a protrusion (not shown) formed on a back surface of the elongate central portion 24 that is adapted to extend an elongate slot 38 formed in the elongate central portion 34 of the second member 30.

Figure 2C:
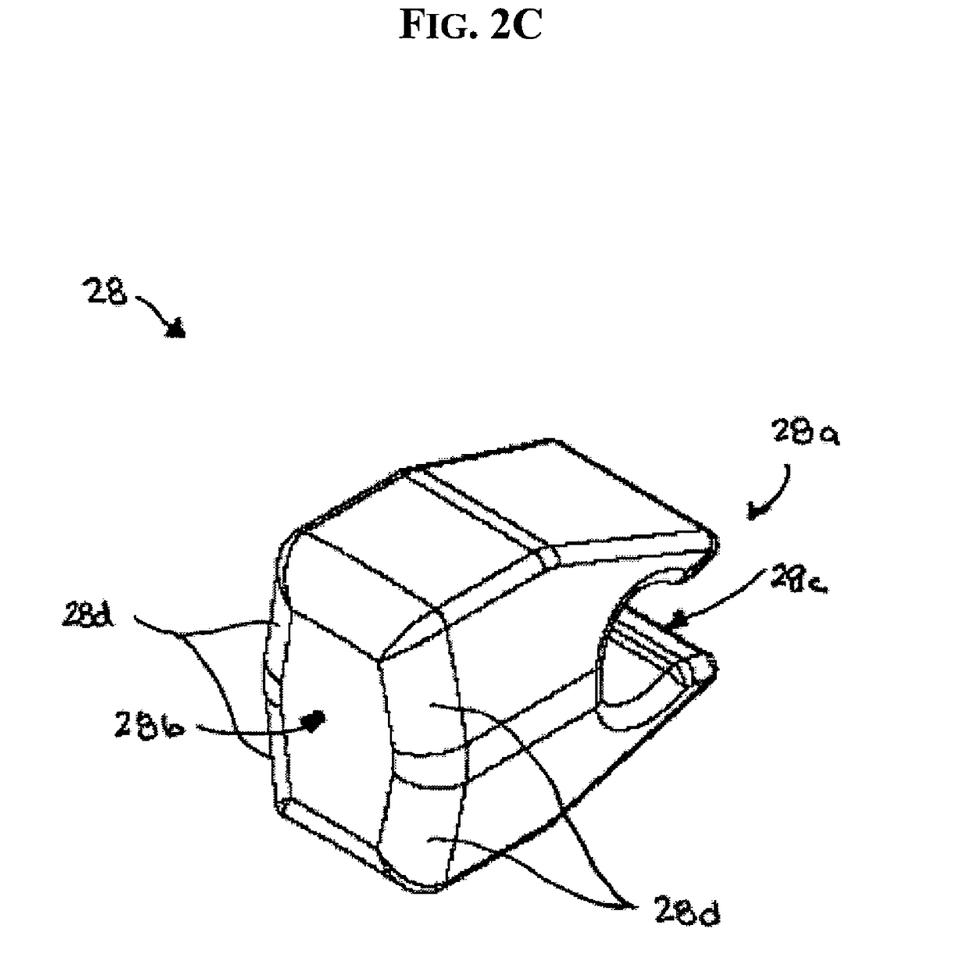
FIG. 2C is a distal perspective view of the connecting element shown in the FIG. 2A.

As noted above, the distal end 24b, or some other portion of the elongate central portion 24 of the first member 20, can be adapted to mate to the second member 30. While a variety of mating techniques can be used, in one exemplary embodiment, shown in FIG. 2B, the first member 20 includes a connecting element 28 coupled thereto and adapted to be slidably received within the elongate slot 38 formed in the central portion 34 of the second member 30. The connecting element 28 can have a variety of configurations, but in one exemplary embodiment, as shown in FIGS. 2B and 2C, the connecting element 28 is freely rotatably attached to the distal end 24b of the central portion 24 of the first member 20. In particular, the distal end 24b can include a bar or rod 26 extending there across, and the connecting element 28 can have a substantially elongate shape with a first end 28a that is adapted to mate to the rod 26, and a second end 28b that is adapted to mate to the second member 30. While various techniques can be used to mate the first end 28a to the rod 26, in one exemplary embodiment as shown the first end 28a includes a recess or cut-out 28c formed therein for receiving the rod 26. The cut-out 28c can be adapted to engage the rod 26 using an interference fit or snap-fit to substantially prevent removal of the connecting element 28 from the rod 26, while still allowing the connecting element 28 to rotate relative to the rod 26. Alternatively, the rod 26 can be passed through the cut-out 28c in the connecting element 28 during manufacturing such that the connecting element 28 is not removable from the rod 26. In use, free rotation of the connecting element 28 relative to the first member 20 allows the connecting element 28 to pivot during slidable movement of the first and second members 20, 30 relative to one another.

As noted above, the second end 28b of the connecting element 28 can be adapted to mate to the elongate central portion 34 of the second member 30. In one exemplary embodiment, the second end 28b can be adapted to slidably mate to the second member 30, and more preferably it can be adapted to be slidably received within a groove or slot 38 formed in the second member 30, as will be discussed in more detail below. Accordingly, the second end 28b can have a shape and size that corresponds to a shape and size of the slot 38 to allow slidable movement thereof within the slot 38. The second end 28b and/or the slot 38 can also have a shape that prevents removal of the connecting element 28 from the slot 38 during use. For example, the second end 28b can taper toward the first end 28a and the slot 38 can likewise be tapered. In another exemplary embodiment, the second end 28b can also be configured to allow some degree of lateral bending thereof within the slot 28. As shown in FIG. 2C, the second end 28b has a diamond or hexagonal shape with angled sides 28d that will allow a certain amount of rotation. While the amount of lateral bending can vary, in one exemplary embodiment that connecting element 28 is adapted to rotate about $\pm 7°$.

The connecting element 28 can also be formed from a variety of materials, but in one exemplary embodiment the connecting element 28 is formed from a material that facilitates sliding of the connecting element 28 within the slot 38, and that will withstand substantial wear over time. Suitable exemplary materials include ultra high molecular weight polyethylene, polyurethane, ceramics, and various biocompatible metals (titanium, stainless steel, cobalt chrome). The slot 38, which forms the bearing surface for the connecting element 28, can also be formed from a material, such as stainless steel, that withstands substantial wear over time. The connecting element 28 and/or the slot 38 can also or alternatively include a surface coating to facilitate movement therebetween The second member 30 of the posterior implant 10 can also have a variety of configurations. In one exemplary embodiment, as shown in more detail in FIG. 3, the second member 30 can have a shape that is similar to an upside-down Y. In particular, the second member 30 can include an elongate central portion 34 having proximal and distal ends 34a, 34b, and opposed arms 32a, 32b extending from opposed sides of the distal end 34b for mating the second member 30 to the inferior vertebra 60i.

Figure 3:
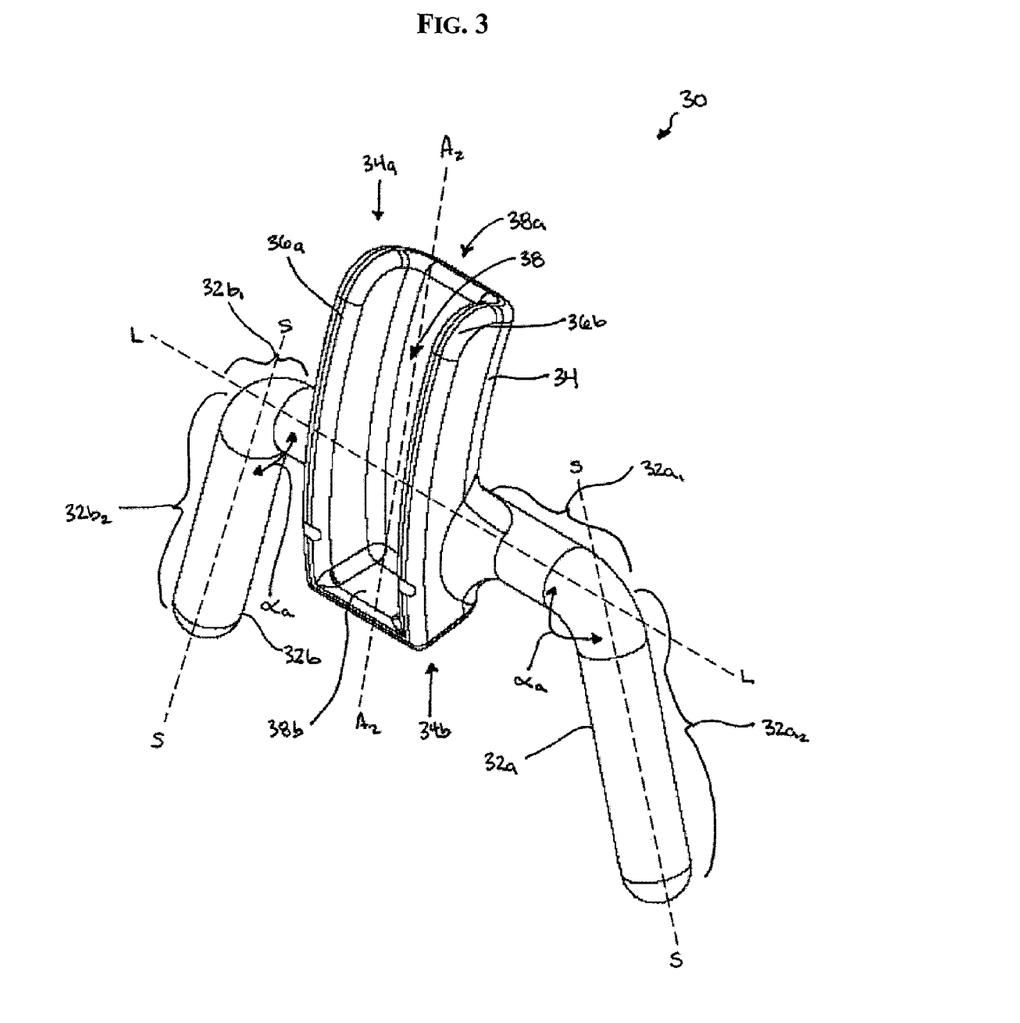
FIG. 3 is a perspective view of the second member of the posterior implant shown in FIGS. 1A and 1B.

As previously discussed above with respect to the first member 20, the opposed arms 32a, 32b can have a variety of configurations and they can be adapted to mate to a variety of bone engaging devices. As shown in FIG. 3, each arm 32a, 32b extends from a location that is adjacent to the distal end 38b of the central portion, and each arm 32a, 32b is substantially L-shaped. In particular, each arm 32a, 32b includes a first portion $32a_1$, $32b_1$ that extends along an axis L in a direction that is substantially perpendicular to a longitudinal axis $A_2$ of the central portion 34, and a second portion $32a_2$, $32b_2$ that distally extends along an axis S at an angle α relative to the first portion $32a_1$, $32b_1$. Such a configuration allows the arms 32a, 32b to mate to opposed pedicles 60c, 60d (FIG. 1A) of the inferior vertebra 60i and to extend between the pedicles 60c, 60d and superior to the spinous process 62 (FIGS. 1A-1B). As previously discussed above with respect to the first member 20, the arms 32a, 32b can be mated to the vertebra 60i using a variety of techniques, but in an exemplary embodiment each arm 32a, 32b is disposed within a receiving member 51c, 51d of a bone screw 50c, 50d and locked thereto using a locking element, such as a locking nut 52c, 52d.

The central portion 34 of the second member 30 can also have a variety of configurations, but in one exemplary embodiment the central portion 34 is adapted to movably mate to the central portion 24 of the first member 20. As previously indicated, the central portion 34 can include an elongate groove or slot 38 formed therein for slidably receiving the connecting element 34. In an exemplary embodiment, the slot 38 is defined by opposed rails 36a, 36b that extend between proximal and distal ends 34a, 34b of the central portion 34. The slot 38 can also include an open proximal end 38a to allow the connecting element 34 to be inserted therein, and a closed distal end 38b to prevent the connecting element 34 from sliding distally there beyond. As previously indicated, the elongate central portion 34 of the second member 30 can also have a substantially spherical surface along the longitudinal axis $A_2$ such that the curvature along the longitudinal axis $A_2$ and the curvature in a direction substantially perpendicular to the longitudinal axis $A_2$ are substantially the same. Such a configuration will allow flexion and lateral bending of the vertebrae 60s, 60i while having full contact between the first and second members 20, 30. In an exemplary embodiment, the curvature of the central portion 34 can be adapted to match a desired envelope of motion, as will be discussed in more detail below.

In use, referring back to FIGS. 1A and 1B, the posterior implant 10 can be used in conjunction with a natural disc or with an artificial disc to control movement of the adjacent vertebrae 60s, 60i relative to one another. In an exemplary embodiment, the posterior implant 10 is used with a spinal prosthesis having an artificial disc that is freely movably relative to the vertebrae 60s, 60i. FIGS. 1A and 1B illustrate one exemplary embodiment of a spinal prosthesis 60 having a superior endplate 62s that is adapted to be positioned adjacent to an endplate of the superior vertebra 60s, and an inferior endplate 62i that is adapted to be positioned adjacent to an endplate of the inferior vertebra 60i. An artificial disc 64 is disposed between the endplates 62s, 62i, and it has substantially convex superior and inferior surfaces that are received within corresponding substantially concave surfaces of the endplates 62s, 62i. As a result, the artificial disc 64 is adapted to slidably and rotatably move relative to the endplates 62s, 62i. The artificial disc can, however, include an outer lip or rim 66 formed thereon that will limit rotation of the disc, thereby limiting flexion, extension, lateral bending, anterior-posterior shear, etc. of the vertebrae 60s, 60i. Accordingly, the spinal prosthesis 60 will have an envelope of motion, which will be discussed in more detail below. One exemplary spinal prosthesis is the Charité™ Artificial Disc available from DePuy Spine, Inc.

Once the spinal prosthesis 60 is implanted between the adjacent vertebrae 60s, 60i, the posterior implant 10 can be implanted by coupling the first and second members 20, 30 to the adjacent vertebrae 60s, 60i, e.g., using bone screws 50a-d, as previously described. While the order in which the parts are implanted in not particularly relevant, in an exemplary embodiment the second member 30 is mated to bone screws 50c, 50d, which are implanted in the inferior vertebra 60i. The locking nuts 52c, 52d can then be loosely mated to the receiving members 51c, 51d of the bone screws 50c, 50d to loosely couple the second member 30 to the vertebra 60i. The first member 20 can then be mated to bone screws 50a, 50b, which are implanted in the superior vertebra 60s, and the connecting element 28 attached to the first member 20 can be positioned within the slot 38 in the second member 30. The locking nuts 52a, 52b can then be loosely mated to the receiving members 51a, 51b of the bone screws 50a, 50b to loosely couple the first member 20 to the vertebra 60s. The first and second members 20, 30 can then be adjusted as necessary, and once properly positioned, the locking nuts 52s-d can be tightened to lock the first and second members 20, 30 in a fixed position relative to the vertebrae 60s, 60i. In use, the connecting element 28 will slide within the slot 38 in the second member 30 as the vertebrae 60s, 60i flex and extend relative to one another. The connecting element 28 can also rotate within the slot in a clockwise and counterclockwise direction during lateral bending of the vertebrae 60s, 60i. Rotation of the vertebrae 60s, 60i relative to one another can be substantially prevented as the connecting element 28 will not be allowed to move side-to-side within the rails 36a, 36b on the second member 30. Some minor rotation (e.g., ±2 degrees) may occur by providing a gap between the connecting element 28 and side walls 36a and 36b.

As previously indicated, in one exemplary embodiment the posterior implant 10 has an appropriate size and curvature that is based on a desired envelope of motion. The desired envelope of motion of the posterior implant 10 can be determined by the envelope of motion of the particular disc, e.g., spinal prosthesis 60 and the desired location of the posterior implant 10 relative to the disc (which may be based on the size of the patient). The location of the posterior implant 10 relative to the disc can be determined through imaging such as fluoroscope or radiograph. Once determined, a posterior implant 10 having the appropriate size and curvature can be selected from a kit containing multiple implants 10 or varying sizes and configurations.

Figure 4A:
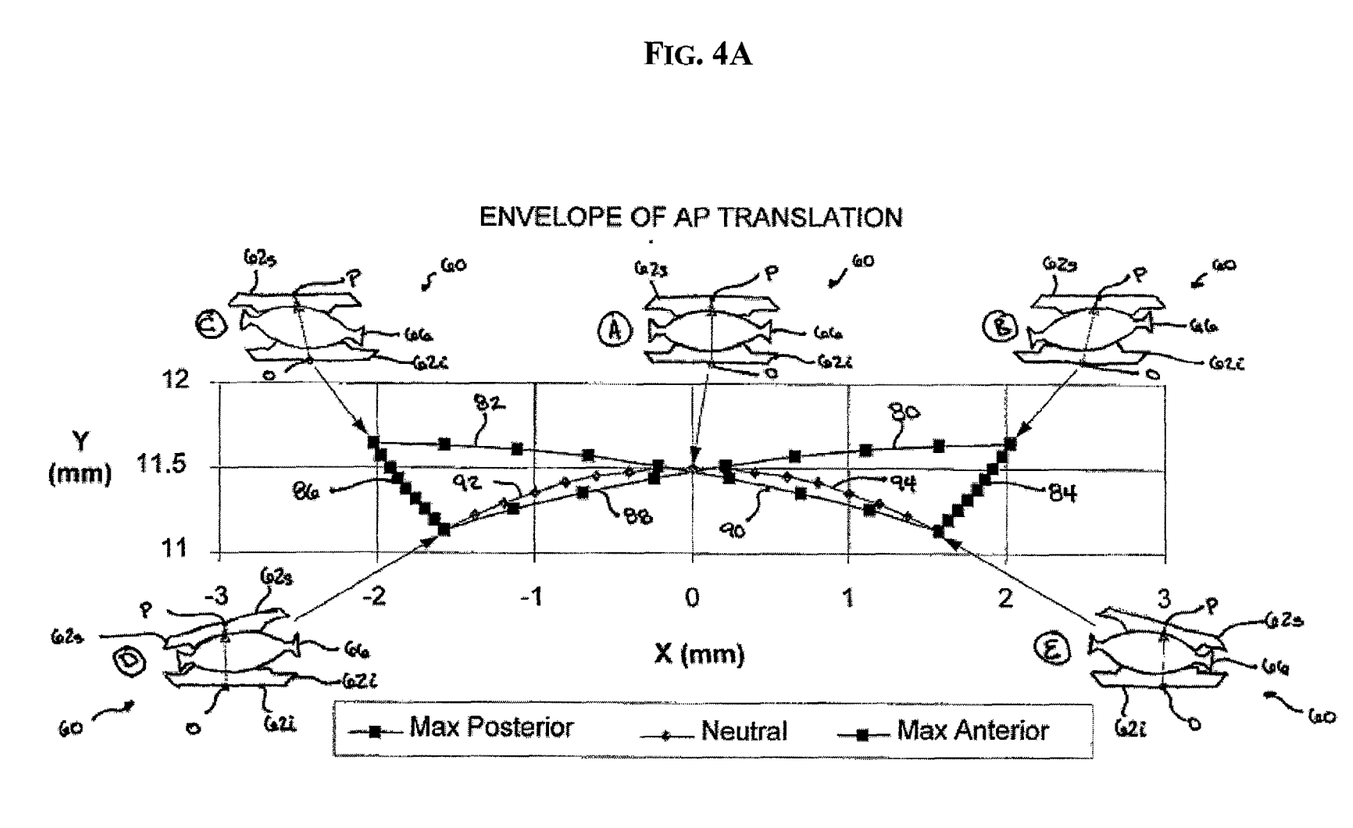
FIG. 4A is a chart showing an envelope of motion of one exemplary embodiment of a spinal prosthesis.

FIG. 4A illustrates the envelope of motion of spinal prosthesis 60. The envelope of motion for a reference point P on the superior endplate 62s is determined by tracking the point P relative to a fixed reference point O on the inferior endplate 62i between extreme positions allowed by the spinal prosthesis 60. As shown, the point P on the superior endplate 62s is movable between a neutral position A in which the superior endplate 62s is parallel and aligned with the inferior endplate 62i, and the core 66 is also centered between the parallel endplates 62s, 62i; positions B and C in which the superior endplate 62s is parallel to the inferior endplate 62i, but it has fully translated in an anterior direction and a posterior direction due to rotation of the core 66 which may be caused by anterior and posterior shear; and positions D and E in which the superior endplate 62s is fully pivoted toward the inferior endplate 62i in an anterior direction and a posterior direction due to flexion and extension.

During movement of the superior endplate 62s between the various positions A-E, the coordinates of point P are charted. In particular, in the neutral position A, point P on the superior endplate 62s is at 0 on the X axis, and at 11.5 on the Y axis (i.e., the coordinates of point P are 0 mm, 11.5 mm). From this neutral position A, the superior endplate 62s can translate in an anterior direction to the position indicated by reference B, and in a posterior direction to the position indicated by reference C. This motion is indicated by lines 80 and 82 and is representative of anterior-posterior shear. As the point P on the superior endplate translates or moves along the X axis in an anterior direction to position B or in a posterior direction to position C, the shape of the core 66 causes point P to move farther apart from point O along the Y axis as the core 66 rotates. From the neutral position A the spinal prosthesis 60 can also move to positions D and E as a result of flexion and extension of the vertebrae. As the superior endplate 62s rotates from position A to position D or position E, the core 66 rotates half the amount of 62s (neutral motion) causing point P on the superior endplate 62s to translate along the X axis and to move closer to the inferior endplate 62i, as indicated by the Y axis. This motion is represented by lines 92 and 94. The spinal prosthesis 60 can also move from position C to position D, as indicated by line 86, and from position B to position E, as indicated by line 84. As shown, during these transitions the core 66 causes point P on the superior endplate 62s to move back toward the inferior endplate 62i along the X and Y axes. In sum, lines 80-94 define the envelope of motion for point P of the spinal prosthesis 60. A person skilled in the art will appreciate that the envelope of motion of the spinal prosthesis 60 will vary depending on the particular shape, size, and configuration of the spinal prosthesis 60.

Figure 4B:
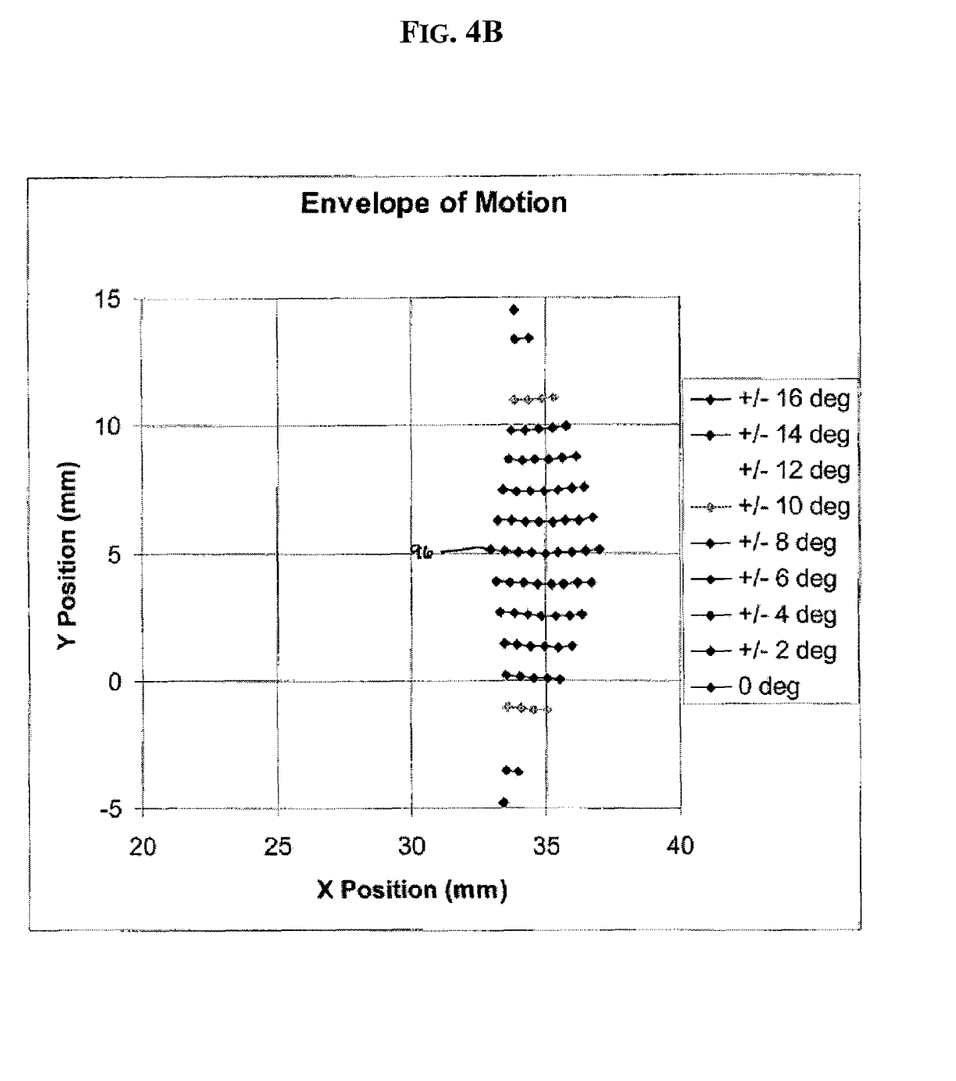
FIG. 4B is a chart showing a desired envelope of motion of a posterior implant to be used with the spinal prosthesis shown in FIG. 4A.

Similarly, an envelope of motion can be defined for a different point attached to spinal prosthesis 60. FIG. 4B tracks the movement of a point located at the facet joint, hereinafter referred to as the facet point, attached to the superior vertebra 60s. In the example shown in FIG. 4B, the facet point is believe to have the coordinates 35 mm, 5 mm, such that the facet point is a distance of 35 mm along the X axis from reference point O on the inferior endplate 62i, and a distance of 5 mm along the Y axis from reference point O on the inferior endplate 62i. The chart illustrates the movement of the facet point relative to reference point O on the inferior endplate 62i of the spinal prosthesis 60 during flexion and extension. In particular, the chart illustrates movement of the facet point when the superior and inferior endplates 62s, 62i are positioned at 0° relative to one another, as indicated by line 96, and in ±2° increments up to ±16°, which is the maximum amount of flexion/extension allowed by the spinal prosthesis 60 of certain size. Together, these lines define the allowed envelope of motion of A posterior implant 10 to be used in conjunction with the spinal prosthesis 60. Accordingly, the allowed envelope of motion can be used to select a posterior implant 10 having an envelope of motion that is within the allowed envelope of motion. In particular, the posterior implant 10 can have a size and curvature that is within the size limits and curvature shown in FIG. 4B. The facet point can be determined by imaging, e.g., using fluoroscopy, the spinal prosthesis 60 after it is positioned between adjacent vertebrae. Furthermore, the posterior implant 10 can also be located and orientated through imaging, e.g., using fluoroscopy.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed as new and desired to be protected by Letters Patent of the United States is:

1. A method for stabilizing the posterior element in adjacent vertebrae, comprising:
    implanting a disc prosthesis between adjacent vertebrae such that the disc prosthesis is movable relative to the adjacent vertebrae, the disc prosthesis having an envelope of motion;
    determining a location on the adjacent vertebrae to couple a posterior implant to the adjacent vertebrae based on the envelope of motion of the disc prosthesis, the location being selected such that the posterior implant has an envelope of motion that is within the envelope of motion of the disc prosthesis; and
    coupling the posterior implant to the location on the adjacent vertebrae to control flexion, extension, and lateral bending of the adjacent vertebrae relative to one another, and to substantially limit axial rotation of the adjacent vertebrae relative to one another.

2. The method of claim 1, wherein the envelope of motion of the disc prosthesis is determined based on a size and location of the disc prosthesis disposed between the adjacent vertebrae.

3. The method of claim 1, wherein coupling the posterior implant to the adjacent vertebrae comprises coupling a first member to a vertebra, and coupling a second member to an adjacent vertebra, the first and second members being movably coupled to one another.

4. The method of claim 1, wherein implanting the disc prosthesis between adjacent vertebrae comprises positioning first and second endplates with the artificial disc disposed therebetween between the adjacent vertebrae, and wherein coupling the posterior implant to the adjacent vertebrae comprises coupling first and second members to the adjacent vertebrae, the first and second members being movably coupled to one another.

5. The method of claim 1, wherein the posterior implant is selected from a kit comprising a plurality of posterior implants having different sizes and curvatures.

6. The method of claim 1, wherein determining the location on the adjacent vertebrae to couple the posterior implant to the adjacent vertebrae comprises imaging the adjacent vertebrae after the disc prosthesis is implanted therebetween.

* * * * *